United States Patent
Forsell

(10) Patent No.: US 6,551,235 B2
(45) Date of Patent: Apr. 22, 2003

(54) IMPLANTABLE PUMP

(75) Inventor: Peter Forsell, Menzingen (CH)

(73) Assignee: Potencia Medical AG, Baar (CH)

( * ) Notice: Subject to any disclaimer, the term of this patent is extended or adjusted under 35 U.S.C. 154(b) by 20 days.

(21) Appl. No.: 09/918,939

(22) Filed: Aug. 1, 2001

(65) Prior Publication Data

US 2002/0022759 A1 Feb. 21, 2002

Related U.S. Application Data

(60) Provisional application No. 60/301,142, filed on Jun. 28, 2001.

(51) Int. Cl.[7] ................................................. A61F 2/02
(52) U.S. Cl. ........................................................ 600/30
(58) Field of Search .............................. 600/30, 31, 16, 600/593; 417/417, 491, 492, 500; 604/67, 891.1, 131, 141, 133; 607/32; 128/831, 843, 855, DIG. 25

(56) References Cited

U.S. PATENT DOCUMENTS

| | | | | | |
|---|---|---|---|---|---|
| 4,428,365 A | * | 1/1984 | Hakky | ........................ | 600/31 |
| 4,966,533 A | * | 10/1990 | Uchida et al. | ............... | 417/417 |
| 5,100,304 A | * | 3/1992 | Osada et al. | ................. | 417/417 |
| 6,067,991 A | * | 5/2000 | Forsell | ........................ | 128/899 |
| 6,210,347 B1 | * | 4/2001 | Forsell | ........................ | 600/32 |

* cited by examiner

Primary Examiner—Eric F. Winakur
Assistant Examiner—Brian Szmal

(57) ABSTRACT

A pump for medical implantation is disclosed which comprises a housing forming a cylindrical cavity, a cylindrical piston movable in the cavity for providing fluid communication between the cavity and channels opening to the cavity, and a motion device for magnetically rotating the piston and moving it back and forth to provide fluid flow between the cavity and the channels. Advantageously, the cylindrical piston is movable as a loose body in the cavity, and thus, functions as a valve. As a result, the pump of the invention is simple and very reliable, since it is devoid of traditional valves. When implanted in a patient, the pump can be used to pump hydraulic fluid between a reservoir and a hydraulic constriction device also implanted in a patient to thereby operate the device and form a the constriction of a passage of the patient's organ. Also disclosed is a method for laparascopically implanting the hydraulically operable implant together with the pump in a patient's abdomen.

24 Claims, 2 Drawing Sheets

IMPLANTABLE PUMP

This application claims the benefit of Provisional Application No. 60/301,142, filed Jun. 28, 2001, the entire content of which is hereby incorporated by reference in this application.

BACKGROUND AND SUMMARY OF THE INVENTION

The present invention relates to a pump and methods for implanting the pump in a patient's body. More specifically, the present invention relates to a pump of small size and few moving elements, in order to make the pump reliable and suitable for implantation.

Small pumps currently available comprise various kinds of valves. However, such valves may malfunction after some time making the pump unreliable and therefore not suited for implantation. Implanted pumps used together with implants definitely need to be able to stay in the human body for a very long time and still work without problems. There are valve-less pumps available, such as gear pumps. However, prior valve-less pumps are not suited for implantation, because they are complicated, expensive and leaky.

An object of the present invention is to provide a small, simple and reliable pump suited for implantation in a human body.

Another object of the invention is to provide an apparatus including the pump, for restricting the flow in a passage of a patient's organ.

Yet another object of the invention is to provide methods for implanting the pump together with hydraulic devices served by the pump.

Accordingly, in accordance with a first aspect of the invention, there is provided a pump for medical implantation, comprising a housing forming a cylindrical cavity having a closed end and an open end opposite the closed end, the housing being provided with a first fluid channel opening into the cavity at a first location and a second fluid channel opening into the cavity at a second location circumferentially displaced from the first location, a cylindrical piston movable in the cavity and having an indentation for providing fluid communication between the cavity and the first channel, when the piston is turned into a first turning position, and for providing fluid communication between the cavity and the second channel, when the piston is turned into a second turning position, and a motion device for moving the piston back and forth to provide fluid flow between the cavity and any of the channels and for rotating the piston back and forth between the first and second positions.

Advantageously, the cylindrical piston is movable as a loose body in the cavity. Thus, the loose piston also functions as a valve. As a result, the pump of the invention is simple and very reliable, since it is devoid of traditional valves.

Alternatively, the housing may be provided with more than two fluid channels opening into the cavity of the housing, wherein the motion device is capable of rotating the piston so that the indentation of the piston can provide fluid communication between the cavity and any one of the channels.

In accordance with an embodiment of the invention, the pump comprises a rod, which is movable by magnetic force, the rod being rigidly connected to the piston and extending through the open end of the cylindrical cavity, wherein the motion device comprises a first solenoid for generating a first magnetic force to move the rod axially back and forth, so that the piston performs suction and pressure strokes. Preferably, the motion device further comprises a second solenoid for generating a second magnetic force to rotate the rod back and forth so that the piston is moved between the first and second positions. As a result, the piston has no mechanical connection with anything outside the housing, because it is only moved by magnetic forces generated by the two solenoids. Accordingly, since the piston with its rod is the only element of the pump that is movable, this embodiment is extremely reliable. In this embodiment, an energizer, including, for example, a battery and pulse generating means, may be provided for powering the solenoids with electric pulses. As a result, the pump will have low energy consumption. Only one electric pulse through the further solenoid may be sufficient to provide a shift of the piston between the first and second positions of the piston.

The rod may be magnetic and orientated such that it exerts a force on the piston in the direction opposite the axially moving direction of the piston, when the solenoid is energized to pull the piston in the suction stroke, and exerts a force on the piston in the same direction as the axially moving direction of the piston, when the solenoid is energized to push the piston in the pressure stroke. As a result, the total axial force acting on the piston will be reduced when the piston performs a suction stroke, and increased when the piston performs a pressure stroke.

Generally, the housing and piston are made of ceramic material and the clearance between the piston and the housing is less than 5 $\mu$m, which provides a practically gas-tight seal between the piston and the housing.

In accordance with a second aspect of the invention, there is provided an apparatus for restricting the flow in a passage of a patient's organ, comprising a hydraulic constriction device implanted in the patient to form a constriction of the passage, the constriction device being operable to change the constriction of the passage, a reservoir implanted in the patient for supplying hydraulic fluid for the operation of the hydraulic constriction device, and the pump of the present invention as described above implanted in the patient for pumping hydraulic fluid between the reservoir and the hydraulic constriction device to operate the hydraulic constriction device to change the constriction of the passage.

The apparatus may be used for treating a number of different diseases. Thus, it may be used for an obese patient or a patient suffering from reflux and heartburn disease, wherein the hydraulic constriction device forms a constriction of the patient's stomach or esophagus. It may be used for a urinary or anal incontinent patient, wherein the hydraulic constriction device forms a constriction of the urethra or rectum. It may also be used for an impotent patient, wherein the hydraulic constriction device forms a constriction of the patient's exit penile veins.

The pump of the invention can be made very small, which makes it particularly suited for implantation. Thus, in accordance with a third aspect of the invention, there is provided a method for laparascopically implanting a hydraulically operable implant together with the pump as described above in a patient's abdomen, the method comprising the steps of: a) insufflating the patient's abdomen to form a pneumoperitoneum; b) inserting at least one laparascopic trocar into the abdomen; c) using the trocar to introduce the hydraulic implant and pump into the abdomen; and d) operating a tool via the trocar to fix the hydraulic implant and pump at selected locations in the abdomen and to provide a hydraulic connection between the pump and the hydraulic implant.

The method may further comprise step e): post-operatively controlling the implanted pump in a non-invasive manner for the operation of the hydraulic implant. Step (e) may be performed by using a wireless remote control for controlling the pump and may further comprise transmitting wireless energy from outside the patient's body for use in the power of the implanted pump.

Alternatively, the pump may be subcutaneously implanted. Thus, there is also provided a method for implanting a hydraulically operable implant together with the pump as described above in a patient's abdomen, the method comprising the steps of: a) insufflating the patient's abdomen to form a pneumoperitoneum; b) inserting at least one laparascopic trocar into the abdomen; c) using the trocar to introduce the hydraulic implant into the abdomen; d) operating a tool via the trocar to fix the hydraulic implant at a selected location in the abdomen; e) subcutaneously implanting the pump; and f) providing a hydraulic connection between the pump and the hydraulic implant. Also in this alternative method the implanted pump may be post-operatively controlled in a non-invasive manner for the operation of the hydraulic implant, suitably by using a wireless remote control for controlling the pump, and wireless energy may be transmitted from outside the patient's body for use in the power of the implanted pump.

BRIEF DESCRIPTION OF PREFERRED EMBODIMENTS OF THE INVENTION

Figure 1:
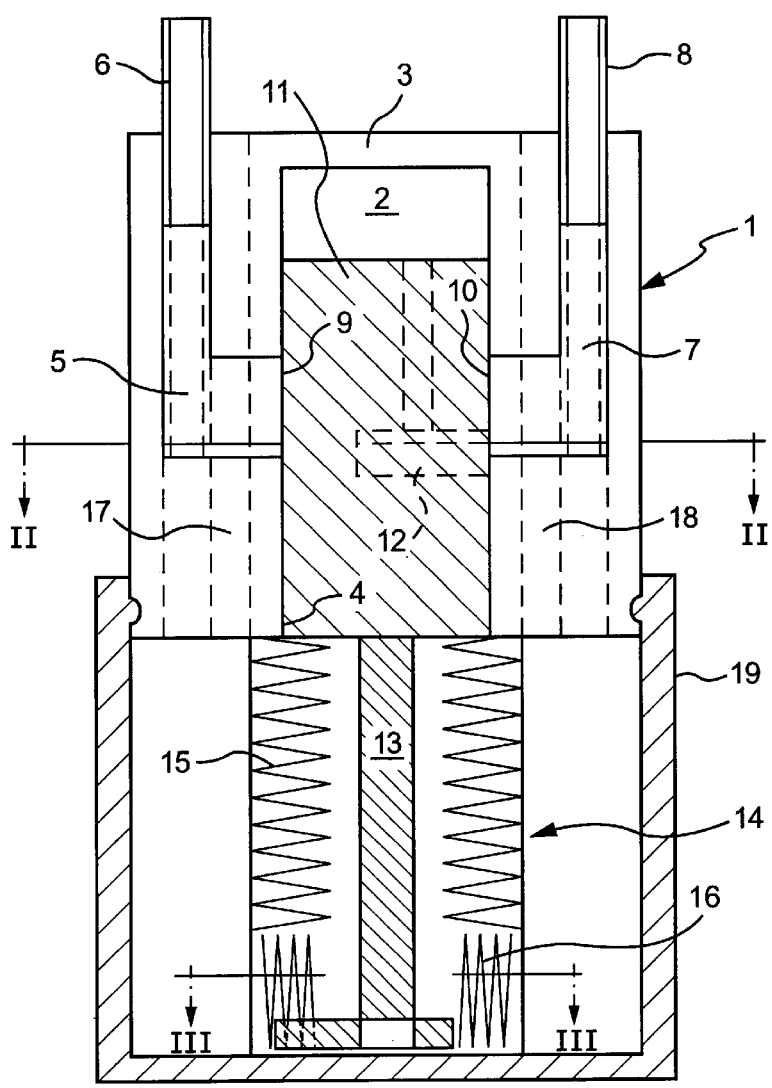
FIG. 1 is a longitudinal cross-section through an embodiment of the pump according to the present invention.
Figure 2:
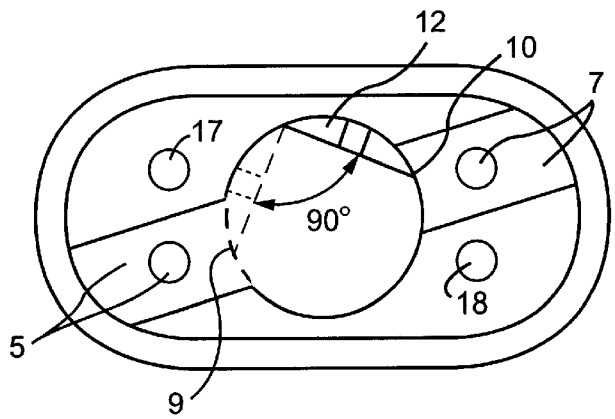
FIG. 2 is a cross-section along the line A—A in FIG. 1.

FIG. 1 shows a pump according to the present invention comprising a housing 1 of ceramic material forming a cylindrical cavity 2 having a closed end 3 and an open end 4 opposite the closed end 3. The housing 1 is provided with a first fluid channel 5 extending from the cavity 2 to a connection pipe 6 and a second fluid channel 7 extending from the cavity 2 to another connection pipe 8. The first channel 5 opens into the cavity 2 at a first location 9 and the second channel 7 opens at a second location 10 circumferentially displaced from the first location 9. A cylindrical piston 11 of ceramic material is movable as a loose body in the cavity 2 and has a T-shaped indentation 12 for providing fluid communication between the cavity 2 and the first channel 5, when the piston 11 is turned into a first turning position, and for providing fluid communication between the cavity 2 and the second channel 7, when the piston 11 is turned into a second turning position. FIG. 2 illustrates the piston 11 situated in the second position. In FIG. 2 the piston 11 turned 90° from the second position into the first position is illustrated by the T-shaped indentation 12 indicated in broken lines.

A rod 13 is rigidly connected to the piston 11 and extends through the open end 4 of the cavity 2. A solenoid motion device 14 is provided for moving the piston 11 back and forth to provide fluid flow between the cavity 2 and any of the channels 5 and 7 and for rotating the piston 11 back and forth between the first and second positions. The motion device 14 comprises a first solenoid 15 extending along the rod 13 to generate a first magnetic force to move the rod 13 and the piston 11 connected thereto axially back and forth, and a second solenoid 16 extending around the rod 13 to generate a second magnetic force to rotate the rod 13 back and forth so that the piston 11 is turned between the first and second positions. The housing 1 is provided with through bores 17 and 18 for electric lines to be connected to the solenoids 15 and 16. A cover 19 encloses the solenoid motion device 14 and is attached to the housing 1.

When fluid is to be pumped from connection pipe 8 to connection pipe 6, the pump is operated in the following manner. With the piston 11 in the second turning position shown in FIG. 2, the solenoid 15 is energized so that the piston 11 performs a suction stroke, whereby fluid is sucked from the connection pipe 8 via the channel 7 and indentation 12 into the cavity 2. When the suction stroke is finished, the solenoid 16 is energized to turn the piston 11 from the second turning position to the first turning position. Then, the solenoid 15 is energized so that the piston 11 performs a pressure stroke, whereby fluid is pressed from the cavity 2 via the indentation 12 and channel 5 into the connection pipe 6. When fluid is to be pumped in the opposite direction, i.e., from connection pipe 6 to connection pipe 8, the pump is operated so that the above described operation steps are performed in the reverse order while the solenoid is energized so that the piston first performs a suction stroke and then a pressure stroke.

Figure 3:
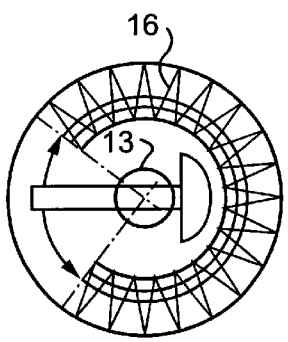
FIG. 3 is a cross-section along the line B—B in FIG. 1.
Figure 4:
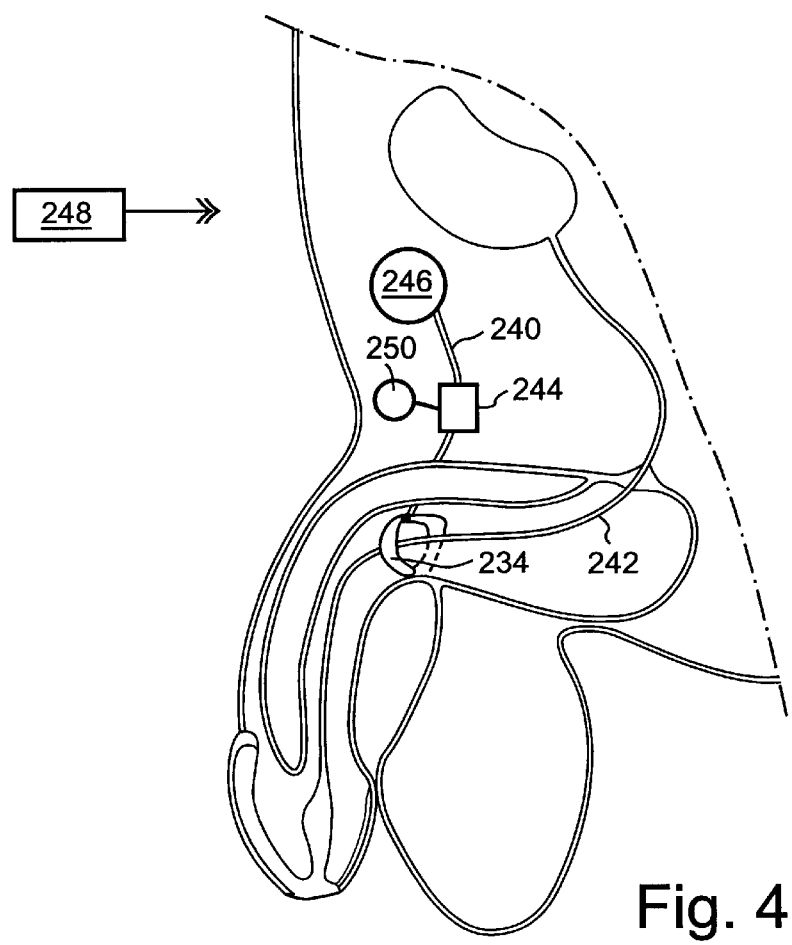
FIG. 4 schematically illustrates an apparatus of the invention for restricting the urine flow in the urethra of a urinary incontinent patient.

FIG. 4 shows an apparatus for restricting the urine flow in the urethra 242 of a urinary incontinent patient, including a hydraulic constriction device 234 applied on the urethra 242, an implanted reservoir 246 for supplying hydraulic fluid for the operation of the constriction device 234, a tubing 240 extending between the reservoir 246 and the constriction device 234 and an implanted pump 244 for pumping hydraulic fluid between the reservoir 246 and the constriction device 234 via the tubing 240. The pump 244 is of the type described above in connection with FIGS. 1–3.

Figure 5:
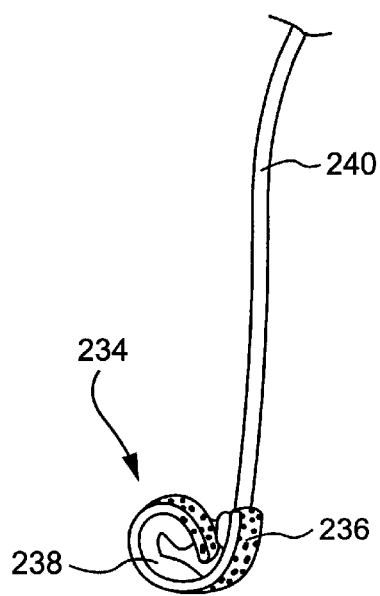
FIG. 5 illustrates a detail of the apparatus shown in FIG. 4.

The constriction device 234 includes a band member 236 forming a loop and an inflatable balloon 238 provided on the inner side of the loop forming band member 236, see FIG. 5. When the pump 244 is powered to transfer hydraulic fluid from the reservoir 246 to the constriction device 234, the balloon 238 is inflated and constricts the urethra 242, so that urine is prevented from leaking from the patient's urine bladder through the urethra 242. When the patient desires to urinate, the pump 244 is powered to transfer hydraulic fluid from the constriction device back to the reservoir 246, so that the urethra 242 is released.

A remote control 248 held by the patient transmits wireless energy for the power of the pump 244 and also transmits control signals for controlling the pump 244. An implanted energizer 250 transforms the transmitted wireless energy into electric energy for powering the solenoids 13, 16 of the pump 244.

What is claimed is:

1. A pump for medical implantation, comprising:

a housing forming a cylindrical cavity having a closed end and an open end opposite said closed end, said housing being provided with a first fluid channel opening into said cavity at a first location and a second fluid channel opening into said cavity at a second location circumferentially displaced from said first location, a cylindrical piston movable in said cavity and having an indentation for providing fluid communication between said cavity and said first channel, when said piston is turned into a first turning position, and for providing fluid communication between said cavity and said second channel, when said piston is turned into a second turning position, and a motion device for moving said piston back and forth to provide fluid flow between said cavity and any of said channels and for rotating said piston back and forth between said first and second positions.

2. A pump according to claim 1, further comprising a rod, which is movable by magnetic force, said rod being rigidly connected to said piston and extending through said open end of said cylindrical cavity, wherein said motion device comprises a first solenoid for generating a first magnetic force to move said rod axially back and forth, so that the piston performs suction and pressure strokes.

3. A pump according to claim 2, wherein said motion device comprises a second solenoid for generating a second magnetic force to rotate said rod back and forth so that said piston is moved between said first and second positions.

4. A pump according to claim 2, further comprising an energizer for powering said solenoid with electric pulses.

5. A pump according to claim 2, wherein said rod is magnetic and orientated such that it exerts a force on the piston in the direction opposite the axially moving direction of the piston, when the solenoid is energized to pull the piston in the suction stroke, and exerts a force on the piston in the same direction as the axially moving direction of the piston, when the solenoid is energized to push the piston in the pressure stroke.

6. A pump according to claim 1, wherein the housing and the piston are made of to ceramic material.

7. A pump according to claim 6, wherein the clearance between the piston and the housing is less than 5 $\mu$m.

8. A pump according to claim 1, wherein the cylindrical piston is movable as a loose body in said cavity.

9. A method for laparascopically implanting in a patient's abdomen a hydraulically operable implant, together with the pump as claimed in claim 1, the method comprising the steps of:
   a) insufflating the patient's abdomen to form a pneumoperitoneum;
   b) inserting at least one laparascopic trocar into the abdomen;
   c) using the trocar to introduce the hydraulic implant and pump into the abdomen; and
   d) operating a tool via the trocar to fix the hydraulic implant and pump at selected locations in the abdomen and to provide a hydraulic connection between the pump and the hydraulic implant.

10. A method according to claim 9, further comprising step e): post-operatively controlling the implanted pump in a non-invasive manner for the operation of the hydraulic implant.

11. A method according to claim 10, wherein step (e) is performed by using a wireless remote control for controlling the pump.

12. A method according to claim 10, wherein step (e) further comprises transmitting wireless energy from outside the patient's body for use in powering the implanted pump.

13. A method for implanting in a patient's abdomen a hydraulically operable implant, together with the pump as claimed in claim 1, the method comprising the steps of:
   a) insufflating the patient's abdomen to form a pneumoperitoneum;
   b) inserting at least one laparascopic trocar into the abdomen;
   c) using the trocar to introduce the hydraulic implant into the abdomen;
   d) operating a tool via the trocar to fix the hydraulic implant at a selected location in the abdomen;
   e) subcutaneously implanting the pump; and
   f) providing a hydraulic connection between the pump and the hydraulic implant.

14. A method according to claim 13, further comprising step g): post-operatively controlling the implanted pump in a non-invasive manner for the operation of the hydraulic implant.

15. A method according to claim 14, wherein step (g) is performed by using a wireless remote control for controlling the pump.

16. A method according to claim 14, wherein step (g) further comprises transmitting wireless energy from outside the patient's body for powering the implanted pump.

17. An apparatus for restricting the flow in a passage of a patient's organ, comprising:
   a hydraulic constriction device implanted in the patient to form a constriction of the passage, said constriction device being operable to change the constriction of the passage,
   a reservoir implanted in the patient for supplying hydraulic fluid for the operation of said hydraulic constriction device, and
   a pump implanted in the patient for pumping hydraulic fluid between said reservoir and said hydraulic constriction device to operate said hydraulic constriction device to change the constriction of the passage,
   said pump including
      a housing forming a cylindrical cavity having a closed end and an open end opposite said closed end, said housing being provided with a first fluid channel opening into said cavity at a first location and a second fluid channel opening into said cavity at a second location circumferentially displaced from said first location, said first channel being hydraulically connected to said reservoir, said second channel being hydraulically connected to said hydraulic constriction device,
      a cylindrical piston movable in said cavity and having an indentation for providing fluid communication between said cavity and said first channel, when said piston is turned into a first turning position, and for providing fluid communication between said cavity and said second channel, when said piston is turned into a second turning position, and
      a motion device for moving said piston back and forth to provide fluid flow between said cavity and any of said channels and for rotating said piston back and forth between said first and second positions.

18. An apparatus according to claimed 17, wherein said pump further comprises a rod, which is movable by magnetic force, said rod being rigidly connected to said piston and extending through said open end of said cylindrical cavity, wherein said motion device comprises a first solenoid for generating a first magnetic force to move said rod axially back and forth, so that the piston performs suction and pressure strokes.

19. An apparatus according to claim 18, wherein said motion device further comprises a second solenoid for generating a second magnetic force to rotate said rod back and forth so that said piston is moved between said first and second positions.

20. An apparatus according to claim 18, further comprising an energizer for powering said solenoid with electric pulses.

21. An apparatus according to claim 8, wherein said rod is magnetic and orientated such that it exerts a force on the piston in the direction opposite the axially moving direction of the piston, when the solenoid is energized to pull the piston in the suction stroke, and exerts a force on the piston in the same direction as the axially moving direction of the piston, when the solenoid is energized to push the piston in the pressure stroke.

22. An apparatus according to claim 17, wherein the housing and the piston are made of ceramic material.

23. An apparatus according to claim 22, wherein the clearance between the piston and the housing is less than 5 $\mu$m.

24. An apparatus according to claim 17, wherein the cylindrical piston is movable as a loose body in said cavity.

* * * * *